(12) United States Patent
Hayashi et al.

(10) Patent No.: US 6,439,719 B2
(45) Date of Patent: Aug. 27, 2002

(54) OPHTHALMOLOGICAL APPARATUS

(75) Inventors: Takefumi Hayashi; Kunihiko Hara; Ken Suzuki, all of Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 59 days.

(21) Appl. No.: 09/742,343

(22) Filed: Dec. 22, 2000

(30) Foreign Application Priority Data

Dec. 27, 1999 (JP) .......................................... 11-370848

(51) Int. Cl.⁷ ................................................ A61B 3/14
(52) U.S. Cl. ..................................................... 351/208
(58) Field of Search ............................... 351/205, 206, 351/207, 208, 209, 210, 211, 214, 216, 221, 237, 239, 240, 241, 245

(56) References Cited

U.S. PATENT DOCUMENTS

| 5,532,769 A | 7/1996 | Miwa et al. |
| 5,587,748 A | 12/1996 | Luce et al. |
| 6,334,682 B1 * | 1/2002 | Takai ......................... 351/206 |

FOREIGN PATENT DOCUMENTS

JP 8-010225 1/1996

* cited by examiner

*Primary Examiner*—George Manuel
(74) *Attorney, Agent, or Firm*—Burns, Doane, Swecker & Mathis, LLP

(57) ABSTRACT

An ophthalmological apparatus includes: a main unit section having a movable optical system housing which houses an optical system for shooting or examining an eye to be examined; a manual operation unit manually positioning the main unit section; an alignment chart projection unit projecting onto the eye an chart luminous flux for alignment; a chart detection unit detecting the reflected luminous flux of the chart luminous flux reflected on the eye; an alignment unit moving the optical system housing with respect to the main unit section on the basis of a detection result of the chart detection unit in a case where the main unit section is positioned by the manual operation unit so that the chart detection unit detects the reflected luminous flux; a position information detection unit detecting information about variations in position of the main unit section caused by the manual operation unit during the operation of the chart detection unit; and a correction unit correcting the moving amount of the optical system housing to be moved by the alignment unit on the basis of a detection result of the position information detection unit.

9 Claims, 10 Drawing Sheets

OPHTHALMOLOGICAL APPARATUS

BACKGROUND OF THE INVENTION

1. Field of the Invention

The present invention relates to an ophthalmological apparatus, such as an ocular refractive power measuring device or retinal camera, equipped with an automatic alignment mechanism.

2. Description of the Related Art

In a case where an eye to be examined (hereinafter simply called an "eye") is examined or photographed through use of an ophthalmological apparatus such as an ocular refractive power measuring device or retinal camera, an optical system housing which houses an optical system must be aligned with the eye beforehand. Such alignment of the optical system housing has hitherto been performed by means of an operator manually actuating the optical system housing through manipulation of a joystick or a trackball. However, a recent ophthalmologic apparatus employs an automatic alignment mechanism which automatically aligns an optical system housing with an eye on the basis of alignment information acquired by way of an photoelectric converting element.

Such an automatic alignment mechanism can detect misalignment within a narrow range. Thus, the automatically alignment mechanism can actuate the optical system housing within the narrow range adjacent to a position where alignment of the optical system housing is to be completed (hereinafter called "an alignment detectable range"). Therefore, the operator must manually perform rough alignment of the optical system housing until the optical system housing enters the alignment detectable range, by means of operating manual operation means, such as a joystick, while viewing an anterior chamber image of the eye appearing on a monitor screen. In the ophthalmological apparatus equipped with an automatic alignment mechanism, the optical system housing is provided on the main unit in a movable manner. The alignment of the optical system housing is firstly performed by means of manual movement of the main unit until the optical system housing enters the alignment detectable range. When the optical system housing enters an alignment detectable range as a result of the alignment of the main unit, the automatic alignment mechanism commences operation, thereby automatically completing an alignment operation.

However, since the extent to which the optical system housing is actuated by means of the automatic alignment mechanism is nominal, it is difficult for the operator to determine commencement of operation of the automatic alignment mechanism at a glance. For example, if the automatic alignment mechanism has already commenced operation to actuate the optical system housing, in many cases the operator may continue operating the manual operation means without being aware of commencement of operation of the automatic alignment mechanism, wherewith the operator manually actuates the optical system housing through use of the manual operation means simultaneously with the optical system housing being actuated by the automatic alignment mechanism. The conventional automatic alignment mechanism computes the amount of misalignment and actuates the optical system housing to correct the misalignment on the premise that the manual operation means is not operated from a point in time at which the automatic alignment mechanism commences operation. In the event that operation of the manual operation means is continued and the automatic alignment mechanism actuates the optical system housing simultaneously with actuation of the optical system housing performed by means of operation of the manual operation means, an error arises between the computed amount of alignment and the actual amount of alignment. As a result, the optical system housing is excessively actuated to be out of the alignment detectable range again, thereby resulting in consumption of much time before completion of the alignment operation.

In order to avoid such problems, the ophthalmological apparatus described in Japanese Patent Application Laid-Open No. 10225/1996 is designed such that commencement of operation of the automatic alignment mechanism is informed to the operator by means of a message appearing on a monitor. However, the operator encounters difficulty in stopping operation of the manual operation means just upon receipt of such information. Hence, the optical system housing cannot be actuated by only an appropriate amount, thus resulting in consumption of much time before completion of the alignment.

U.S. Pat. No. 5,587,748 describes an ophthalmological apparatus which electrically revokes drive of the optical system housing based on operation of the manual operation means after the automatic alignment mechanism has commenced operation. However, such a system cannot be applied to a case where the manual operation means is embodied as a mechanical joystick.

SUMMARY OF THE INVENTION

The present invention has been conceived to solve the drawbacks of the conventional art and is aimed at providing an ophthalmological apparatus capable of preventing a delay in completion of the alignment of an optical system housing, which would otherwise be caused when an automatic alignment mechanism actuates the optical system housing simultaneously with manual operation means actuating the optical system housing, even in a case where a mechanical mechanism is adopted as manual operation means.

To attain the above object, according to a first aspect to the invention, there is provided an ophthalmological apparatus including:

a main unit section having a movable optical system housing which houses an optical system for shooting or examining an eye to be examined;

a manual operation unit manually positioning the main unit section;

an alignment chart projection unit projecting onto the eye an chart luminous flux for alignment;

a chart detection unit detecting the reflected luminous flux of the chart luminous flux reflected on the eye;

an alignment unit actuating the optical system housing on the basis of a detection result of the chart detection unit in a case where the main unit section is positioned by the manual operation unit so that the chart detection unit detects the reflected luminous flux, such as to move the optical system housing with respect to the main unit section;

a position information detection unit detecting information about variations in position of the main unit section caused by the manual operation unit during the operation of the chart detection unit; and a correction unit correcting the actuating amount of the optical system housing on the basis of a detection result of the position information detection unit.

Further, according to a second aspect of the invention, in the ophthalmological apparatus of the first aspect, the position information detection unit detects a moving distance of the main unit section between a predetermined reference time and a time after a preset time has elapsed from the predetermined reference time.

In addition, according to a third aspect of the invention, the ophthalmological apparatus of the second aspect, further includes: a notice unit noticing an operator that the detection of the chart detection unit is commenced, wherein the preset time is set so as to correspond to a period from when a notice is issued from the notice unit until the operator stops the operation of the manual operation unit in response to the notice.

Moreover, according to a fourth aspect of the invention, in the ophthalmological apparatus according to third aspect, the preset time is set to be sufficiently longer than an averaged period from when the notice is issued from the notice unit until the operator stops the operation of the manual operation unit in response to the notice.

According to a fifth aspect of the invention, there is provided an ophthalmological apparatus including:

a main unit section having a movable optical system housing which houses an optical system for shooting or examining an eye to be examined;

a manual operation unit manually positioning the main unit section; an alignment chart projection unit projecting onto the eye an chart luminous flux for alignment;

a chart detection unit detecting the reflected luminous flux of the chart luminous flux reflected on the eye;

an alignment unit actuating the optical system housing on the basis of a detection result of the chart detection unit in a case where the main unit section is positioned by the manual operation unit so that the chart detection unit detects the reflected luminous flux, such as to move the optical system housing with respect to the main unit section;

a moving speed detection unit detecting a moving speed of the main unit section caused by the manual operation unit during the operation of the chart detection unit; and a correction unit correcting the actuating amount of the optical system housing on the basis of a detection result of the moving speed detection unit.

Further, according to a sixth aspect of the invention, in the ophthalmological apparatus according to the fifth aspect, the moving speed detection unit detects a moving speed of the main unit section at a predetermined reference time and a moving speed of the main unit section at a time after a preset time has elapsed from the predetermined reference time.

In addition, according to a seventh aspect of the invention, the ophthalmological apparatus according to the sixth aspect, further includes: a notice unit noticing an operator that the detection of the chart detection unit is commenced, wherein the preset time is set so as to correspond to a period from when a notice is issued from the notice unit until the operator stops the operation of the manual operation unit in response to the notice.

Moreover, according to an eighth aspect of the invention, in the ophthalmological apparatus according to the seventh aspect, the preset time is set to be slightly longer than an averaged period from when the notice is: issued from the notice unit until the operator stops the operation of the manual operation unit in response to the notice unit.

According to a ninth aspect of the inveniton, there is provided an ophthalmological apparatus including:

a main unit section having a movable optical system housing which houses an optical system: for shooting or examining an eye to be examined;

a manual operation unit manually positioning the main unit section;

an alignment chart projection unit projecting onto the eye an chart luminous flux for alignment;

a chart detection unit detecting the reflected luminous flux of the chart luminous flux reflected on the eye;

an alignment unit actuating the optical system housing on the basis of a detection result of the chart detection unit in a case where the main unit section is positioned by the manual operation unit so that the chart detection unit detects the reflected luminous flux, such as to move the optical system housing with respect to the main unit section;

a moving speed detection unit detecting a moving speed of the main unit section caused by the manual operation unit during the operation of the chart detection unit; and an actuation permission unit permitting a commencement of the actuation of the optical system housing according to the alignment unit on the basis of a detection result of the moving speed detection unit.

DETAILED DESCRIPTION OF THE PREFERRED EMBODIMENTS

Preferred embodiments of the present invention will be described hereinbelow by taking an ocular refractive power measuring device as an example.

<First Embodiment>

A first embodiment of the present invention will now be described by reference to FIGS. 1 through 7.

Figure 1:
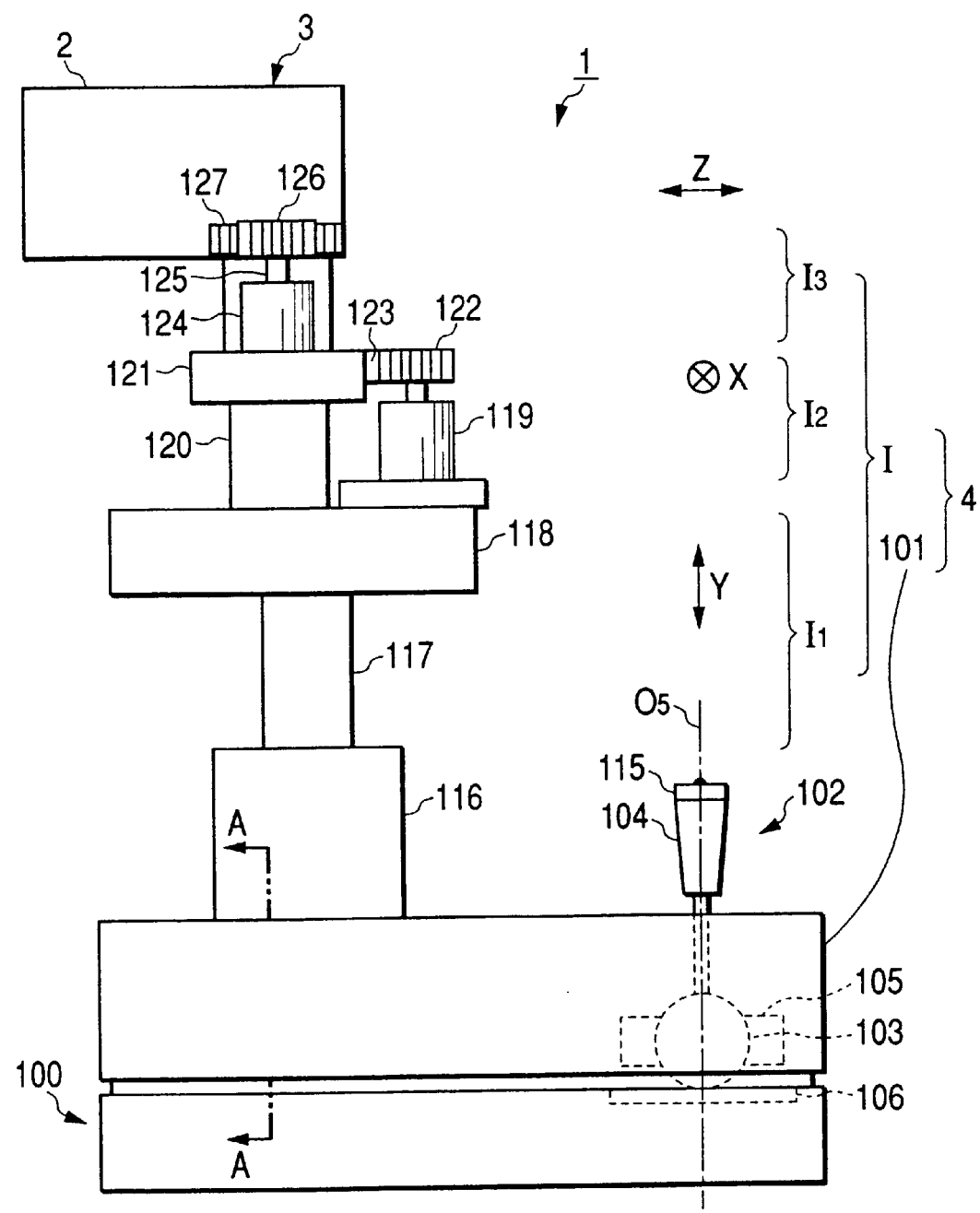
FIG. 1 is an illustration showing the entire construction of an ocular refractive power measuring device according to a first embodiment of the present invention.

FIG. 1 shows the overall configuration of an ocular refractive power measuring device to which the present invention is applied. An ocular refractive power measuring device 1 includes an optical system housing 3, and a main unit section 4 which is provided so that the optical system housing 3 can move in three mutually orthogonal X, Y, and Z directions.

The optical system housing 3 includes an optical system for examining an eye to be examined (hereinafter simply called an "eye") built in a case 2.

Figure 2:
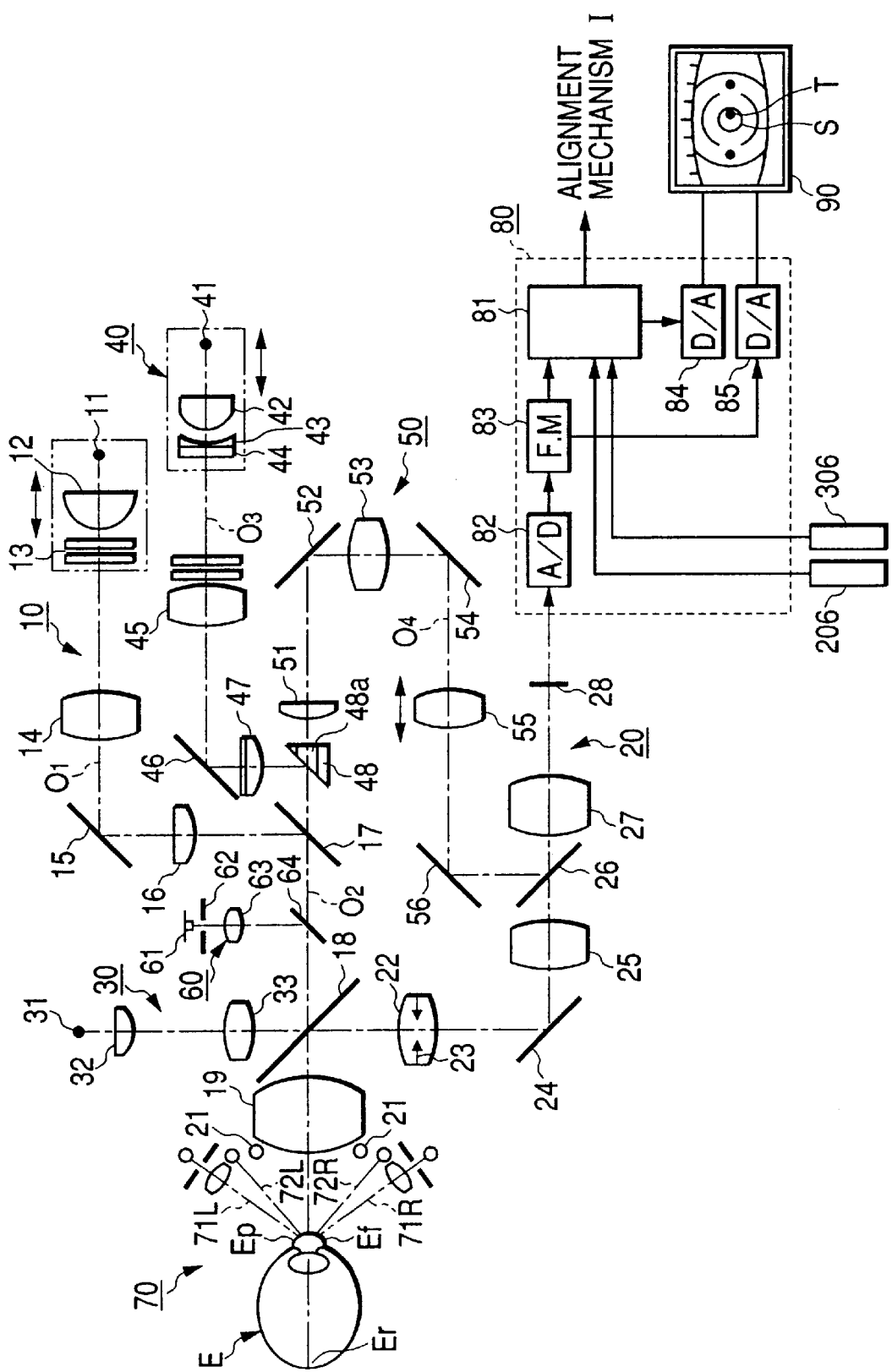
FIG. 2 is a schematic view showing an optical system of a main unit of the ocular refractive power measuring device.
Figure 3:
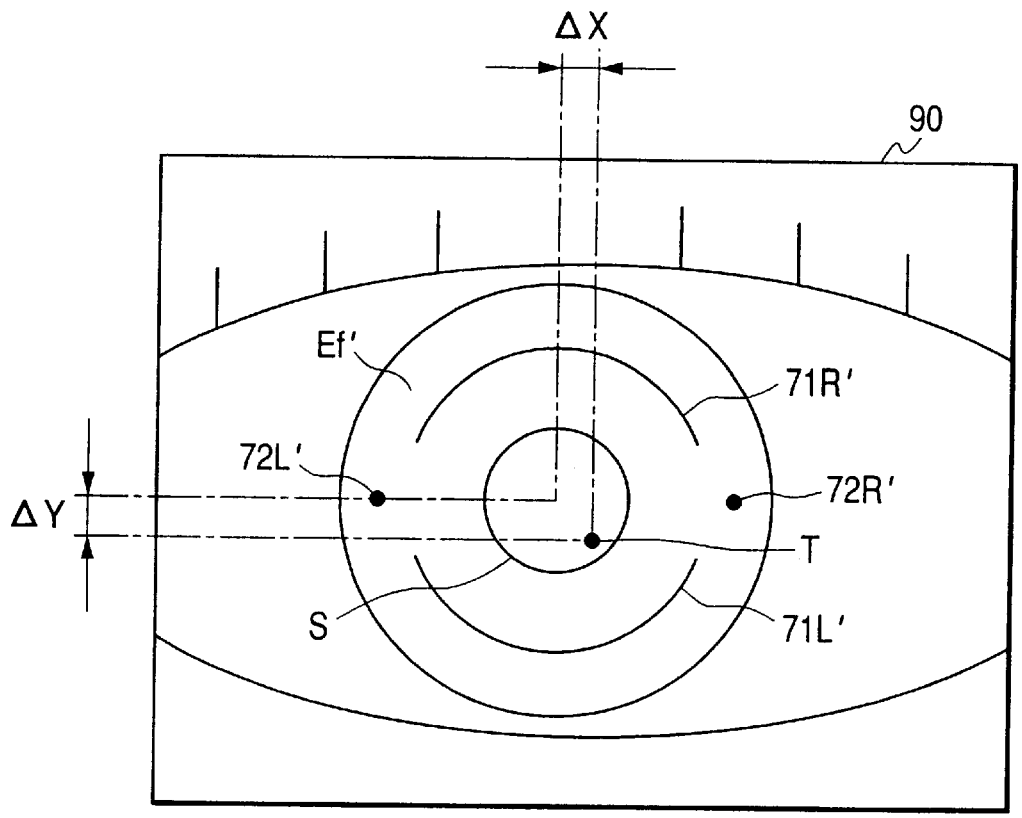
FIG. 3 is an illustration showing a display example of a TV monitor.

As shown in FIG. 2, the optical system housing 3 includes a fixation chart projecting optical system 10; an observing optical system 20; a scale projecting optical system 30; a patterned luminous flux projecting optical system 40; a light-receiving optical system 50; an, alignment chart projecting optical system 60; an working distance detecting system 70; a signal processing/computation section 80; and a TV monitor 90. The fixation chart projecting optical system 10 projects a chart on a fundus Er for fixating and fogging an eye E. The observing optical system 20 is provided to observe an anterior chamber Ef of the eye E. The scale projecting optical system 30 projects a sighting scale on a CCD 28, which is described later. The patterned luminous flux projecting optical system 40 projects a pattern luminous flux onto the fundus Er for measuring the refractive power of the eye E. The light-receiving optical system 50 allows the CCD 28 to receive a luminous flux reflected by the fundus Er. The alignment chart projecting optical system 60 projects on the eye E a chart luminous flux for detecting an alignment state of the optical system housing 3 in the directions (X and Y directions) perpendicular to the optical axis. The working distance detecting system 70 for detecting the working distance between the eye E and the optical system housing 3.

The fixation chart projecting optical system 10 includes a light source 11; a collimator lens 12; a chart plate 13; a relay lens 14; a mirror 15; a relay lens 16; a dichroic mirror 17; a dichroic mirror 18; and an objective lens 19. The light source 11, the collimator lens 12, and the chart plate 13 are assembled into a single unit. The unit can be moved integrally along an optical axis $O_1$ of the fixation chart projecting optical system 10.

Visible light emitted from the light source 11 is converted to a parallel luminous flux by means of the collimator lens 12. The parallel luminous flux passes through the chart plate 13 provided with a target for fixating and fogging the eye E. The luminous flux which has passed through the chart (hereinafter referred to as a "target luminous flux") passes through the relay lens 14 and is reflected by the mirror 15. The target luminous flux further passes through the relay lens 16 and is reflected by the dichroic mirror 17. The thus-reflected target luminous flux passes through the dichroic mirror 18 and the objective lens 19 along the principal optical axis $O_2$ of the optical system housing 3 so as to be guided to the eye E. By means of moving the unit including the light source 11, the collimator lens 12, and the chart plate 13, the fixation chart projecting optical system. 10 can fixate and fog the eye E.

The observing optical system 20 includes a light source 21, the objective lens 19, the dichroic mirror 18, a relay lens 22, a diaphragm 23, a mirror 24, a relay lens 25, a dichroic mirror 26, an image forming lens 27, and the CCD 28.

The luminous flux emitted from the light source 21 is directly applied onto the anterior chamber Ef of the eye E. The luminous flux reflected by the anterior chamber Ef is reflected at the dichroic mirror 18 by way of the objective lens 19. The luminous flux penetrates through the diaphragm 23 while simultaneously passing through the relay lens 22. After having been reflected by the mirror 24, the luminous flux passes through the relay lens 25 and the dichroic mirror 26, thereby forming an image on the CCD 28 by means of the image forming lens 27. As a result, an anterior chamber image Ef' of the eye E is formed on an imaging surface of the CCD 28. A video signal delivered from the CCD 28 is outputted to the TV monitor 90, by way of the signal processing/computation section 80 (see FIG. 3).

The scale projecting optical system 30 includes a light source 31; a collimator lens 32; a relay: lens 33; the dichroic mirror 18; the relay lens 22; the diaphragm 23; the mirror 24; the relay lens 25; the dichroic mirror 26; the image forming lens 27; and the CCD 28. The collimator lens 32 is equipped with a sighting scale.

The luminous flux emitted from the light source 31 is converted into a parallel luminous flux (hereinafter referred to as a "sighting scale luminous flux") when the luminous flux is transmitted through the collimator lens 32. The thus-converted converted luminous flux passes through the relay lens 33, the dichroic mirror 18, the relay lens 22, and the diaphragm 23 and is reflected by the mirror 24. The luminous flux reflected from the mirror 24 passes through the relay lens 25 and the dichroic mirror 26 and is converged into an image on the CCD 28 by means of the image forming lens 27. Consequently, the TV monitor 90 displays the sighting scale S along with the anterior chamber image Ef'. During measurement of the refractive power of the eye to be performed after the optical system housing 3 has been aligned with the eye E, the ocular 15 refractive power measuring device 1 extinguishes the light sources 21 and 31, thereby preventing the CCD 28 from receiving light. Alternatively, a shutter may be provided in the optical path extending from the dichroic mirror 18 to the dichroic mirror 26, thereby shielding the CCD 28 from light.

The patterned luminous flux projecting optical system 40 includes a light source 41; a collimator lens 42; a conical prism 43; a ring chart plate 44; a relay lens 45; a mirror 46; a relay lens 47; a bored prism 48; the dichroic mirror 17; the dichroic mirror 18; and the objective lens 19. The light source 41, the collimator lens 42, the conical prism 43, and the ring chart plate 44 are assembled into a single unit. These elements can be moved in an integrated fashion along the optical axis $O_3$ of the patterned luminous flux projecting optical system 40. The light source 41 and the ring chart plate 44 are located in an optically conjugative position. A ring-shaped pattern (omitted from the drawings) is formed on the ring chart plate 44. The ring chart plate 44 is disposed on an optically conjugative position relative to the pupil Ep of the eye E.

The luminous flux emitted from the light source 41 is converted to a parallel luminous flux bymeans of the collimator lens 42. The thus-converted luminous flux passes through the conical prism 43 and is guided to the ring chart plate 44. The luminous flux which has been guided to the ring chart plate 44 passes through a pattern provided thereon, wherewith the luminous flux becomes a patterned luminous flux. The patterned luminous flux is reflected by the bored prism 48 by way of the relay lens 45, the mirror 46, and the relay lens 47. After having passed through the dichroic mirrors 17 and 18 along the optical axis $O_2$, the thus-reflected patterned luminous flux is converged into an image on the fundus Er by means of the objective lens 19.

The light-receiving optical system 50 includes the objective lens 19; the dichroic mirror 18; the dichroic mirror 17; a bored portion 48a of the bored prism 48; a relay lens 51; a mirror 52; a relay lens 53; a mirror 54; a focusing lens 55; a mirror 56; the dichroic mirror 26; the imaging lens 27; and the CCD 28. The focusing lens 55 is arranged so as to move along the optical axis $O_4$ of the light-receiving optical system 50 in association with the light source 41, the collimator lens 42, the conical prism 43, and the ring chart plate 44, which move in an integrated fashion along the optical axis $O_3$ of the patterned luminous flux projecting optical system 40.

The luminous flux is guided to the fundus Er by the patterned luminous flux projecting optical system 40. After having been converged by the objective lens 19, the luminous flux which has been reflected by the fundus Er passes through the dichroic mirrors 18 and 17 and penetrates through the bored portion 48a of the bored prism 48. The patterned luminous flux which has passed through the bored portion 48a passes through the relay lens 51 and is reflected by the mirror 52. The thus-reflected luminous flux passes through the relay lens 53 and is reflected by the mirror 54. The thus-reflected luminous flux passes through the focusing lens 55 and is reflected by the mirror 56 and the dichroic mirror 26, to thereby form an image on the CCD 28 bymeans of the imaging lens 27. As a result, a pattern image is formed on the imaging surface of the CCD 28.

The alignment chart projecting optical system 60 includes an LED 61; a pinhole 62; a collimator lens 63; a half mirror 64; the dichroic mirror 18, and the objective lens 19.

A chart luminous flux for alignment is projected toward the cornea of the eye E. The chart luminous flux which has been projected by the alignment chart projecting optical system 60 is reflected by the cornea of the eye E. The thus-reflected luminous flux forms an alignment chart image T on the imaging surface of the CCD 28 by means of the light-receiving optical system 50. While viewing the anterior chamber Ef' appearing on the TV monitor 90, the operator performs a rough alignment operation such that the pupil enters the inside of the sighting scale S. When the optical system housing 3 enters the alignment detectable range, the automatic alignment mechanism commences operation. In this respect, there will be provided a detailed description later.

The working distance detecting system 70 includes infinite-distance charts projecting systems 71R and 71L for projecting charts at an infinite distance, and finite-distance charts projecting systems 72L and 72R for projecting charts from a finite distance. The infinite-distance charts projecting systems 71L and 71R are provided symmetrically with respect to the optical axis $O_2$, as in the finite-distance charts projecting systems 72L and 72R. Chart luminous fluxes projected from the four charts projecting systems 71L, 71R, 72L, and 72R undergo reflection on cornea of the eye E. The thus-reflected luminous fluxes form chart images 71L', 71R', 72L', and 72R' on the imaging surface of the CCD 28 by way of the light-receiving optical system 50. The working distance detecting system 70 determines that a working distance becomes optimal for measurement, when the four chart images 71L', 71R', 72L', and 72R' are arranged in a predetermined positional relationship. When the operator performs rough adjustment of the working distance such that the anterior chamber Ef' displayed on the TV monitor 90 is focused, the automatic alignment mechanism automatically performs fine adjustment of the distance.

The signal processing/computation section 80 includes a control circuit 81, an analog-to-digital converter 82, a frame memory 83, a digital-to-analog converter 84, and a digital-to-analog converter 85. The control circuit 81 is connected to the CCD 28 by way of the analog-to-digital converter 82 and the frame memory 83. Further, the control circuit 81 is connected to the TV monitor 90 by way of the digital-to-analog converter 84. The TV monitor 90 is connected to the frame memory 83 by way of the digital-to-analog converter 85. The video signal which has been output from the CCD 28 and stored in the frame memory 83 is displayed directly on the TV monitor 90 or is displayed on the TV monitor 90 after having been processed by the control circuit 81.

Turning again to FIG. 1, the main unit section 4 is placed on top of a base 100 which constitutes the base of the ocular refractive power measuring device 1 and is mounted on a level surface. The main unit section,4 is equipped with a hollow mount 101 provided above the base 100 and an alignment mechanism I attached to an upper portion of the mount 101. A joystick 102 serving as manual operation means is provided to the mount 101. By means of the operator skewing the joystick 102 fore and aft or right and left, the mount 101 is moved in Z direction (i.e., fore and aft) and X direction(right and left) with reference to the base 100.

Figure 4:
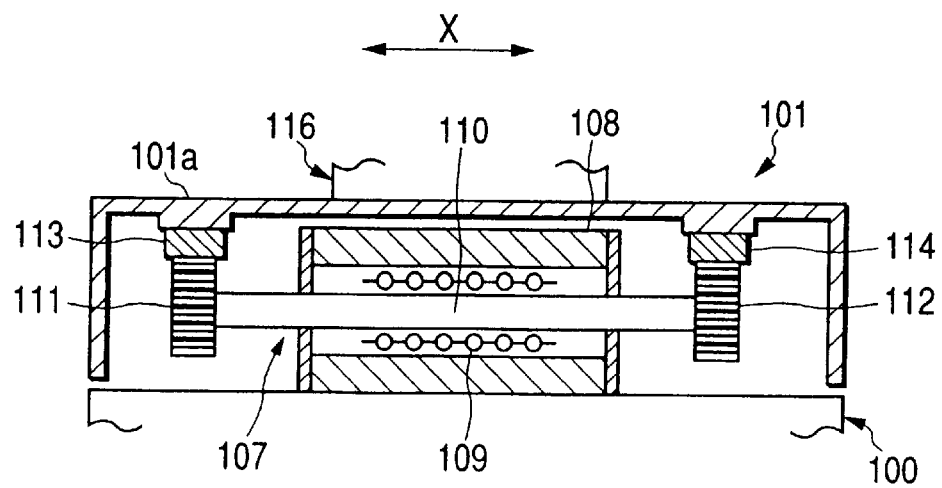
FIG. 4 is a cross-sectional view taken along line A—A shown in FIG. 1.

More specifically, the joystick 102 includes a joystick main body 104 having a spherical section 103 on a lower portion thereof and a ball bearing 105 for retaining the spherical section 103 from the side. The base 100 is further provided with a slide plate 106 which comes into contact with the spherical section 105 from below. A slide guide mechanism 107 shown in FIG. 4 is provided in the mount 101.

The slide guide mechanism 107 includes a guide pipe 108 which is mounted on the base 100 and extends laterally, and a movable shaft 110 which is inserted into the guide pipe 108 and is retained by a bearing 109. The movable shaft 110 can move smoothly in X direction while being guided by the guide pipe 108.

A pinion 111 is provided on one end of the movable shaft 110, and a pinion 112 is provided on the other end of the movable shaft 110. Racks 113 and 114 are provided on the lower surface of a top board 110a of the mount 101 so as to extend fore and aft. The rack 113 is meshed with the pinion 111, and the rack 114 is meshed with the pinion 112. A stopper (not shown) is attached to respective sides of the racks 113 and 114 so as not to disengage the pinions 111 and 112 from the corresponding racks 113 and 114, even when force is applied to the movable shaft 110 in the X direction.

The operator actuates the joystick main body 104 fore and aft and right and left so as to rotate the spherical section 103 over the slide plate 106. As a result, the mount 101 moves fore and aft and right and left with reference to the base 100. In association with movement of the mount 101, the optical system housing 3 also moves fore and aft and right and left (i.e., in X and Z directions) with reference to the base 100. At this time, the racks 113 and 114 are moved while being guided by the corresponding pinions 111 and 112, which rotate along with the movable shaft 110. Consequently, the mount 101 is moved and guided fore and aft (in Z direction). The movable shaft 110 retained by the bearing 109 is moved in the axial direction while being guided by the; guide pipe 108. Thus, the mount 101 is guided and moved the right and left (i.e.; in X direction).

A rotary operation section 115 capable of rotating about the axis $O_5$ is provided on top of the joystick 104. The amount of rotations of the rotary operation section 115 is detected by a rotary encoder (not shown). When the operator rotates the rotary operation section 115, an elevation mechanism I1 to be described later is actuated in accordance with the amount of rotations detected by the rotary encoder, wherewith the optical system housing 3 is moved vertically (i.e., in Y direction). When the amount of misalignment ($\Delta Y$) of the optical system housing 3 in the vertical direction attains a predetermined value or less, the signal output from the rotary encoder is disregarded, and further position adjustment of the optical system housing 3 is relegated to the automatic alignment mechanism.

Figure 5:
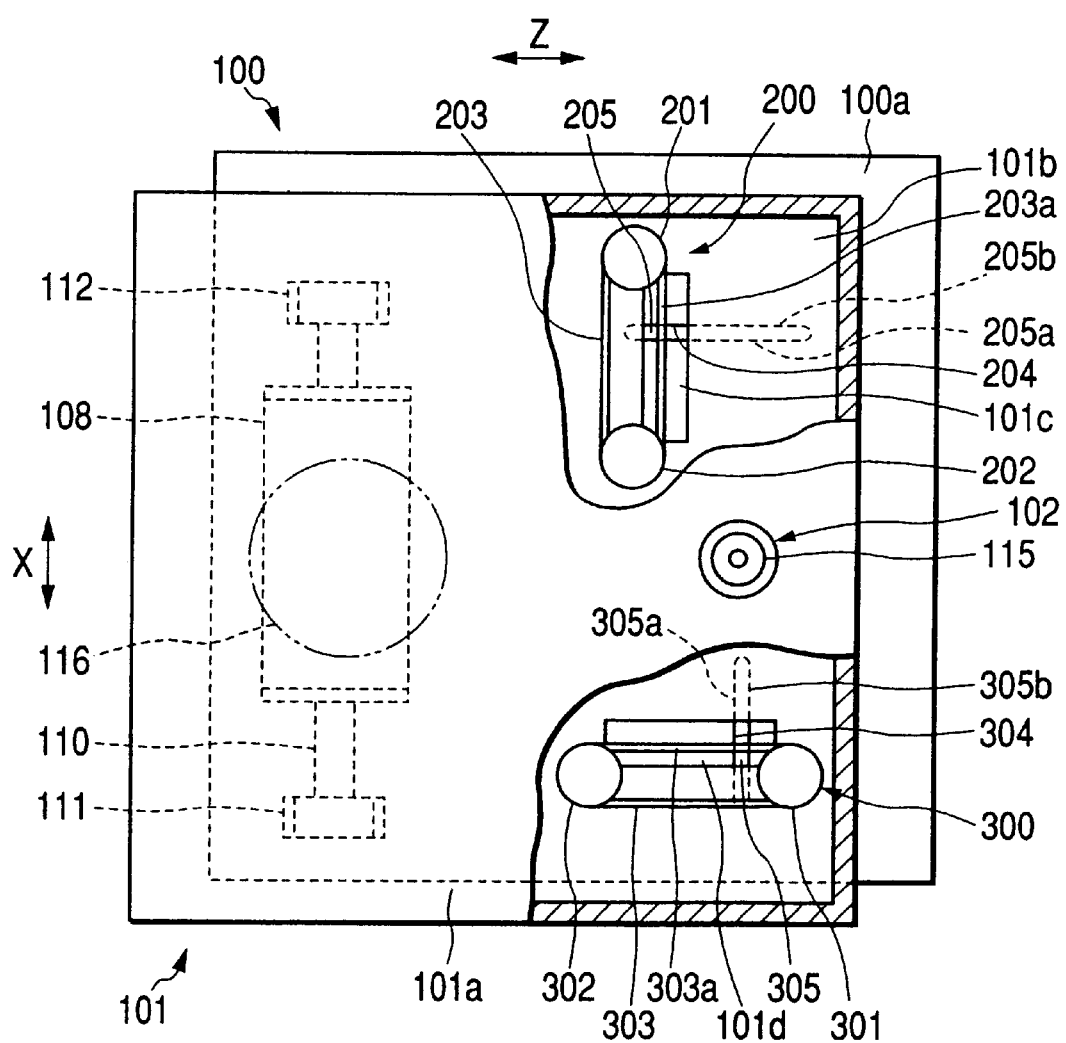
FIG. 5 is a schematic illustration showing each of moving distance detection sections.

The distance over which the mount 101 has moved right and left is detected by an X-direction moving distance detection section 200 shown in FIG. 5, and the distance over which the mount 101 has moved fore and aft is detected by a Z-direction moving distance detection section 300 shown in FIG. 5. The X-direction moving distance detection section 200 includes pulleys 201 and 202; a belt 203; a pin 204; and a guide groove 205. The pulleys 201 and 202 are provided on a bottom plate 101b of the mount 101 in a rotatable manner. The belt 203 is laid between the pulleys 201 and 202. A portion 203a of the belt 203 is aligned parallel with X direction, and the pin 204 is attached to the portion 203a. The pin 204 has a rod shape and extends in the vertical direction (i.e., the direction perpendicular to the sheet of FIG. 5). The pin 204 projects downward from an aperture 101c formed in the bottom plate 101b. The guide groove 205 is formed in an upper surface 100a of the base 100 in parallel with Z direction. The guide groove 205 has a width substantially identical with the outer diameter of the pin 204. The portion of the pin 204 protruding from the aperture 101c is inserted into the guide groove 205.

Similar to the X-direction moving distance detection section 200, the Z-direction moving distance detection section 300 includes pulleys 301 and 302; a belt 303; a pin 304; and a guide groove 305. The pulleys 301 and 302 are provided on the bottom plate 101b of the mount 101 in a rotatable manner. The belt 303 is laid between the pulleys 301 and 302. A portion 303a of the belt 303 is aligned parallel with Z direction, and the pin 304 is attached to the portion 303a. The pin 304 has a rod shape and extends in the vertical direction (i.e., the direction perpendicular to the sheet of FIG. 5). The pin 304 projects downward from an aperture 101d formed in the bottom plate 101b. The guide groove 305 is formed in the upper surface 100a of the base 100 in parallel with X direction. The guide groove 305 has a width substantially identical with the outer diameter of the pin 304. The portion of the pin 304 protruding from the aperture 101d is inserted into the guide groove 305.

In a case where the mount 101 moves in X direction with reference to the base 100, the pin 204 is pressed against either a sidewall 205a or 205b of the guide groove 205. As a result, the pin 204 is moved in a direction opposite to the moving direction of the mount 101, with reference to the bottom plate 101b. In association with movement of the pin 204, the belt 203 rotates the pulleys 201 and 202, and the amount of rotations of at least one of the pulleys 201 and 202 is detected by the rotary encoder 206. A distance over which the mount 101 has moved in X direction is computed by the control circuit 81 (see FIG. 2). At this time, the pin 304 moves only along the guide groove 305, and the Z-direction moving distance detection section 300 is not subjected to any influence. Hence, the moving distance of the mount 101 in Z direction to be detected by the Z-direction moving distance detection section 300 becomes zero.

When the mount 101 moves in Z direction relative to the base 100, the pin 304 is pressed against either the sidewall 305a or 305b of the guide groove 305. As a result, the pin 304 is moved in a direction opposite to the moving direction of the mount 101, with reference to the bottom plate 101b. In association with movement of the pin 304, the belt 303 rotates the pulleys 301 and 302, and the amount of rotations of at least one of the pulleys 301 and 302 is detected by the rotary encoder 306. A distance over which the mount 101 has moved in Z direction is computed by the control circuit 81 (see FIG. 2). At this time, the pin 204 moves only along the guide groove 205, and the X-direction moving distance detection section 200 is not subjected to any influence. Hence, the moving distance of the mount 101 in X direction to be detected by the X-direction moving distance detection section 200 becomes zero.

The alignment mechanism I is connected to the control circuit 81, and constitutes an automatic alignment mechanism of the ocular refractive power measuring device 1. The alignment mechanism I has the elevation mechanism I1; a lateral movement mechanism I2; and a fore-and-aft movement mechanism I3 (see FIG. 1).

The elevation mechanism I1 includes a motor 116 mounted on the mount 101, and a column 117 which is actuated by the motor 116 so as to move in Y direction relative to the mount 101. A table 118 is fixed on top of the column 117.

The lateral movement mechanism I2 includes a motor 119 and a column 120, which are mounted on the table 118. A table 121 is provided on the top of the column 120 so as to be movable in X direction. A pinion 122 is attached to an output shaft of the motor 119, and a rack 123 meshing with the pinion 122 is provided on one side of the table 121. The table 121 is moved in X direction relative to the column 120 by means of drive of the motor 119.

The fore-and-aft movement mechanism I3 includes a motor 124 and a column 125, which are mounted on the table 121. The optical system housing 3 is mounted on top of the column 125 so as to be movable in Z direction. A pinion 126 is attached to an output shaft of the motor 124, and a rack 127 to be meshed with the pinion 126 is provided on one side surface of the case 2 of the optical system housing 3. The optical system housing 3 is moved in Z direction with reference to the column 125 by means of drive of the motor 124.

Figure 6:
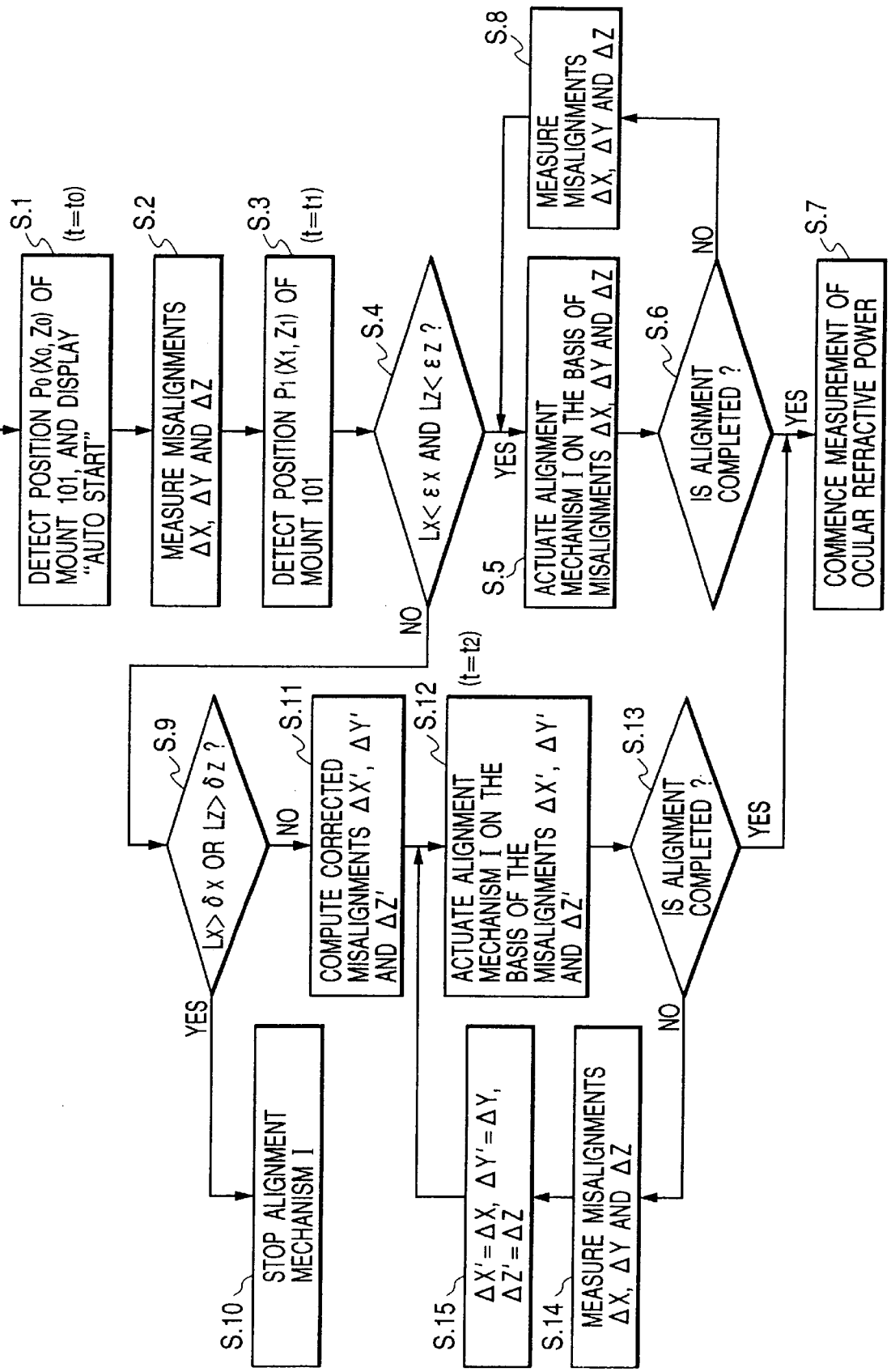
FIG. 6 is a flowchart showing alignment procedures according to the first embodiment.
Figure 7:
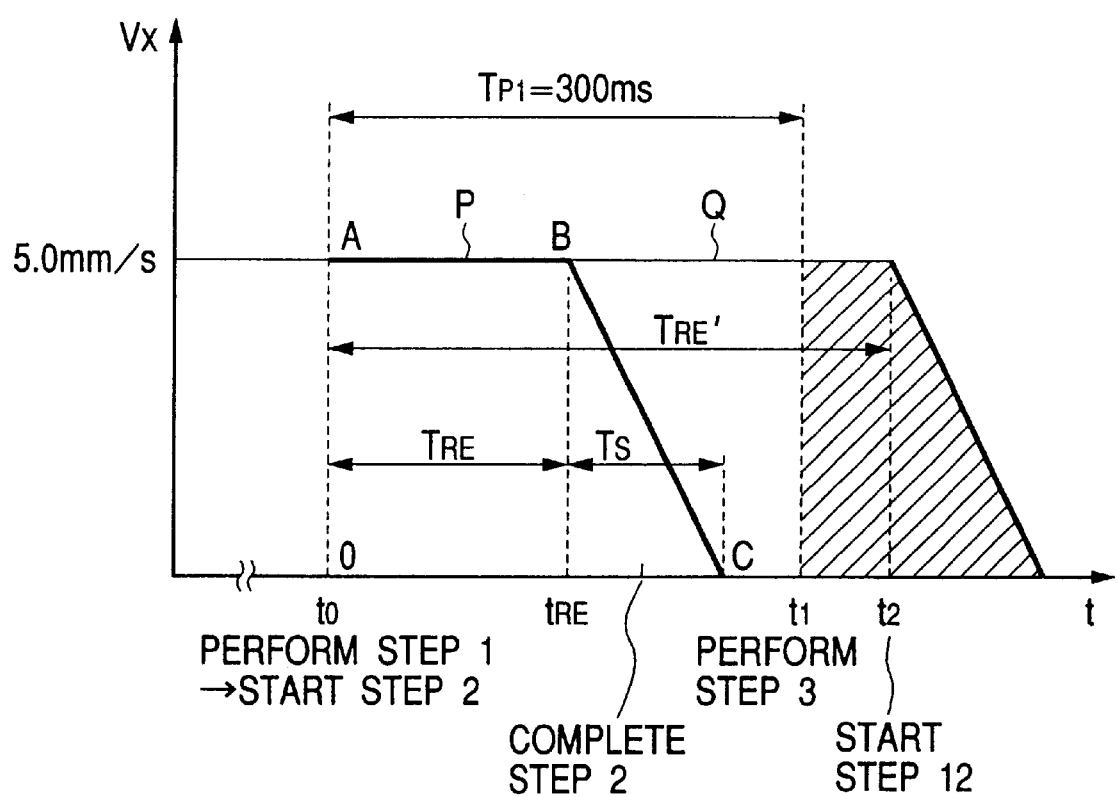
FIG. 7 is a schematic view showing an example of a change in the moving speed of a mount according to the first embodiment.

The operation of the ocular refractive power measuring device 1 according to the first embodiment will be described by reference to FIGS. 6 and 7. FIG. 6 is a flowchart showing procedures for operating the ocular refractive power measuring device 1 according to the present embodiment. FIG. 7 shows an example of variation in the moving speed of the mount 101 with reference to X direction during a period of time in which processing according to the flowchart is performed (the horizontal axis represents time "t" and the vertical axis represents moving speed "Vx"). FIG. 7 is a graph for describing the action of the ocular refractive power measuring device 1 corresponding to a change in the moving speed of the mount 101. This graph does not show results of actual measurement of changes in the moving speed of the mount 101. In the present embodiment, the alignment detectable range of the automatic alignment mechanism is an area:in which the amount of misalignment in each of X, Y, and Z directions is a value of 2 mm or less (the area will hereinafter be referred to as an "alignment detectable range"). Predetermined values $\delta_x$ and $\delta_y$, which are described later are determined on the basis of the this area. The measurement of an ocular refractive power after completion of alignment of the optical system housing 3 is commenced in a case where the amount of misalignment in each of X, Y, and Z directions is a value of 0.5 mm or less. Predetermined values $\epsilon_x$ and $\epsilon_z$, which are described later are determined on the basis of an area in which alignment of the optical system housing 3 is deemed as being completed (the area will hereinafter be referred to as an "alignment completion area").

Step 1 (Abbreviated as S1 in FIG. 6, the Same Also Applies to Other Steps)

Prior to Step 1, the operator aligns the main unit section 4 such that the amount of misalignment ΔX and the amount of misalignment ΔZ become small, by means of actuating the joystick 102. The optical system housing 3 is vertically aligned such that the amount of misalignment ΔY becomes small. When the respective amounts of misalignment ΔX, $\Delta Y$, and $\Delta Z$ are a value of 2 mm or less, processing shifts to step 1, whereby the control circuit 81 commences an automatic alignment operation. In step 1 (reference time $t_0$), the control circuit 81 detects the position Po of the mount 101 (i.e., Xo, Zo) on the basis of signals output from the rotary encoders 206 and 306. Message "AUTO START" appears on the monitor 90, thereby notifying the operator of commencement of automatic alignment operation.

When message "AUTO START" appears on the monitor 90, the operator attempts to stop the operation of the joystick 102. However, the operator cannot stop the operation immediately. Assuming that the operation of the joystick 102 is stopped at time $t_{RE}$ after a certain amount of time $T_{RE}$ (response time) has elapsed from time $t_0$. Even if operation of the joystick 102 is stopped immediately, the mount 101 cannot stop immediately, because of inertial force, and hence continues further movement during a period of Ts.

Step 2

Step 2 is commenced immediately after completion of step 1. In step 2, on the basis of the video signal output from the CCD 28, the control circuit 81 measures the respective amounts of misalignment $\Delta X$, $\Delta Y$ and $\Delta Z$ in the X, Y and Z directions at a certain point in time (i.e., a point in time immediately after the automatic alignment mechanism has become able to detect the alignment of the mount 101).

In a case where a CCD is used as a light-receiving element of the alignment detection system as in the present embodiment, a predetermined number of lines are scanned, to thereby obtain a video signal. A binary-coding operation employing an appropriate threshold value must be performed in order to eliminate unwanted information, such as information about an anterior chamber, from the video signal. Computation of misalignment $\Delta X$, $\Delta Y$, and $\Delta Z$ requires a time of about 200 ms.

Step 3

Step 3 is performed at time $t_1$, by which a preset period of time $T_{P1}$ has elapsed since time $t_0$ at which step 1 was performed. In step 3, the control circuit 81 again detects the position of the mount 101 in accordance with the signals output from the rotary encoders 206 and 306. The position detected in step 3 is set as $P_1(X_1, Z_1)$ so as to be distinguished from positions Po(Xo,Zo) determined in step 1.

Here, the preset period of time $T_{P1}$ is sufficiently longer than an average value of response time $T_{RE}$. Here, the sufficient long time means that if operation of the joystick 102 is stopped within an average period of response time, the moving speed Vx of the mount 101 becomes zero or a value nearly zero when step 3 is performed at that time, in consideration of the moving time Ts due to the inertial force of the mount 101. The average value of response time $T_{RE}$ is set to a value of 150 ms, and a preset time $T_{P1}$ is set to 300 ms.

Step 4

Step 4 is performed immediately after completion of step 3. In step 4, the control circuit 81 compares position $P_o$ determined in step 1 with position $P_1$ determined in step 3. A distance over which the mount 101 has moved during the preset period of time $T_{P1}$ is obtained as information concerning changes in the position of the mount 101 induced by operation of the joystick 102. On the basis of the thus-determined information, a determination is made as to whether or not correction of misalignment is required. The moving distance Lx of the mount 101 in X direction is calculated by $Lx=X_1-X_0$, and the moving distance Lz of the mount 101 in Z direction is calculated by $Lz=Z_1-Z_0$. A determination is made as to whether or not Lx and Lz are smaller than the respective predetermined values $\epsilon_x$ and $\epsilon_z$.

On the basis of the result of determination, a further determination is made as to whether or not the misalignments $\Delta X$ and $\Delta Y$ must be corrected.

Next, there is conceived a case where, the operator moves the mount 101 in X direction at a moving speed of Vx=5.0 (mm/s) at the time of step 1 (i.e., time $t_o$), as indicated by line P (solid lines) shown in FIG. 7, by means of operation of the joystick 102. The operator reacts to appearance of message "AUTO START" on the monitor 90, thereby stopping operation of the joystick 102 after lapse of a time $T_{RE}$=150 (ms). However, the mount 101 has continued to move only Ts=100 (ms) by means of inertial force. In this case, the mount 101 moves in the X direction a distance corresponding to the area of a trapezoid ABCO shown in FIG. 7. Distance Lx over which the mount 101 has moved is obtained as $$\{(150+250) \times 10^{-3}\} \times 5.0/2 = 1.0 \text{ (mm)}.$$

Unless the alignment $\Delta X$ is corrected in consideration of the moving distance Lx, the optical system housing 3 will be excessively actuated automatically on the basis of the uncorrected misalignment $\Delta X$. As a result, the optical system housing 3 will pass by an alignment completion area and must be again actuated in reverse. Thus, a comparatively long period of time must be taken before completion of alignment.

In a case where the response time $T_{RE}$ is a value of, for example, 50 ms or less, or in a case where the moving speed Vx of the mount 101 at time $t_0$ is a value of 1 mm/s or thereabouts and the response time $T_{RE}$ is a value of 150 ms or less, the moving distance Lx of the mount 101 in the X direction (i.e., the area of the trapezoid ABCO) becomes smaller than 0.5 mm. In such a case, even if the misalignment $\Delta X$ without correction is used as the amount of actuation as it is, the optical system housing 3 will not pass by the alignment completion area. The alignment can be completed by means of a single series of operations; that is, driving the alignment mechanism I by detecting the amount of misalignment.

The same also applies to the alignment in the Z direction. In step 4, when the result of determination shows that $Lx<\epsilon x$ and $Lz<\epsilon z$, correction of misalignment $\Delta X$ and $\Delta Z$ is determined to be unnecessary. Then, processing proceeds to step 5. When $Lx \geq \epsilon x$ or $Lz \geq \epsilon z$, the amount of misalignment $\Delta X$ or the amount of misalignment $\Delta Z$ must be corrected. To this end, processing proceeds to step 9.

Step 5

In step 5, the control circuit 81 activates motors 116, 119, and 124 of the alignment mechanism I in accordance with the respective amounts of misalignment $\Delta X$, $\Delta Y$ and $\Delta Z$, thereby moving the optical system housing 3 in the X, Y and Z directions by the amounts corresponding to the amounts of misalignment $\Delta X$, $\Delta Y$, and $\Delta Z$.

Steps 6 through 8

In step 6, the control circuit 81 makes a determination as to whether or not the alignment has been completed as a result of actuation of the alignment mechanism I performed in step 5 (i.e., whether or not the optical system housing 3 has entered an alignment completion area). If it is determined that alignment has been completed, processing proceeds to step 7, in which measurement of the refractive power of the eye is commenced. In contrast, if it is determined that the alignment has not yet been completed, the respective amounts of misalignment $\Delta X$, $\Delta Y$ and $\Delta Z$ are measured in step 8 in the same manner as in step 2. Processing again returns to step 5, in which processing is repeatedly performed according to the same procedures.

Steps 9 and 10

In step 9, the control circuit 81 makes a determination as to whether or not the distances Lx and Lz determined to be Lx≧ϵx or Lz≧ϵz in step 4 is greater than predetermined values $\delta_x$ and $\delta_z$. A determination is made as to whether or not the amounts of misalignment ΔX and ΔZ on the basis of the distances Lx and Lz can be corrected.

Sometimes, a delay arises in stoppage of the operation of the joystick 102 because the operator is inattentive to message "AUTO START". If it occurs, the response time (the response time is expressed as $T_{RE}$' in the drawing for the sake of convenience) is longer than the preset time $T_{P1}$, or shorter than the preset time $T_{P1}$ but close to it as shown by line Q (fine lines) in FIG. 7. In this case, the: moving speed Vx of the mount 101 may not become zero at time $t_2$ at which step S12 to be described later is to be commenced, nor at time $t_1$ at which step 3 is to be performed. In such a case, even if correction is made in the amount of misalignment ΔX by only the amount corresponding to the distance Lx, the amount of correction corresponding to a hatched area shown in FIG. 7 becomes insufficient. In this way, if the amount of correction becomes considerably insufficient, a problem analogous to that mentioned in connection with the conventional art may arise.

The same also applies to the alignment in the Z direction. If in step 9 it is determined that Lx>δx or Lz>δz, it is determined that correction of the misalignment ΔX based on the distance Lx or the misalignment ΔZ based on the distance Lz is determined to have already become impossible. Processing then proceeds to step 10, in which operation of the alignment mechanism I is stopped. A message to that effect is displayed on the monitor 90, thereby prompting the operator to perform operation with care. If it is determined that Lx≧δx and Lz≧δz, processing proceeds to step 11 in order to correct the misalignment ΔX on the basis of the distance Lx and correct the misalignment ΔZ on the basis of the distance Lz.

Step 11

In step 11, in consideration of the fact that an overlap corresponding to the distance Lx or Lz exists between actuation of the optical system housing 3 induced by actuation of the joystick 102 and actuation of the optical system housing 3 induced by the automatic alignment mechanism, the control circuit 81 amends the amounts of misalignment ΔX, ΔY and ΔZ, thereby computing the amended amounts of misalignment ΔX', ΔY' and ΔZ'.

$$\Delta X'=\Delta X-Lx \quad (1)$$

$$\Delta Y'=\Delta Y \quad (2)$$

$$\Delta Z'=\Delta Z-Lz \quad (3)$$

In Eq. (2), the amount of misalignment ΔY is sustained in its present form. The reason for this is that although the rotary operation section 115 enables manual adjustment of the vertical position of the optical system housing 3 (i.e., the position of the optical system housing 3 in Y direction), when the optical system housing 3 enters the alignment detectable range and automatic alignment operation is commenced, operation of the rotary operation section 115 is neglected, in the manner mentioned previously.

Step 12

In step 12, the control circuit: 81 activates the motors 116, 119 and 124 of the alignment mechanism I on the basis of the amounts of misalignment ΔX' ΔY' and ΔZ' determined in the previous step. Thus, the optical system housing 3 is moved in the X, Y, and Z directions by the respective amounts corresponding to the amounts of misalignment ΔX', ΔY' and ΔZ'.

Steps 13 Through 15

In step 13, the control circuit 81 makes a determination as to whether or not the alignment has been completed as a result of operation of the alignment mechanism I performed in the previous step. If it is determined that the alignment has been completed, processing proceeds to step 7, in which measurement of the refractive power of the eye is commenced. In contrast, if it is determined that the alignment has not yet been completed, the respective amounts of misalignment ΔX, ΔY and ΔZ are measured in step 14 in the same manner as in step 12. In step 15, the respective values of misalignment ΔX', ΔY' and ΔZ' are replaced with the respective values of misalignment ΔX, ΔY and ΔZ (i.e., ΔX'=ΔX, ΔY'=ΔY, and ΔZ'=ΔZ). Processing returns to step 12, and processing is repeatedly performed according to the same procedures.

<Second Embodiment>

Figure 8:
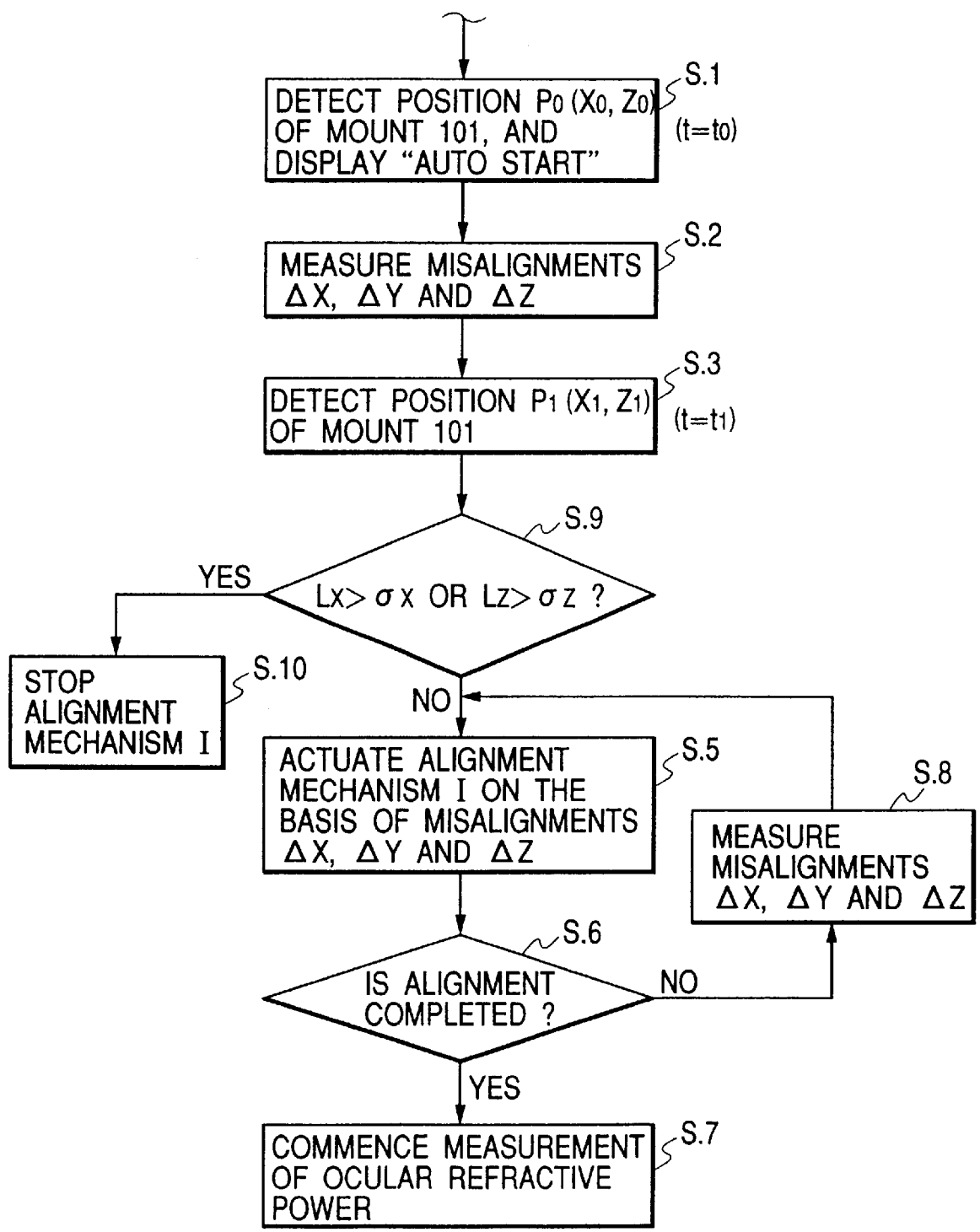
FIG. 8 is a flowchart showing alignment procedures according to a second embodiment of the present invention.

A second embodiment of the present invention will now be described by reference to FIG. 8.

An ocular refractive power measuring device according to the second embodiment is identical in structure with that described in the first embodiment. The only difference lies in a control program of the control circuit 81. FIG. 8 is a flowchart showing the outline of the control program. Steps corresponding to those described in connection with the first embodiment are assigned the same numerals.

The first embodiment has been described for three conditions: that is, (A) when Lx<$\epsilon_x$ and Lz<$\epsilon_z$; (B) when Lx≧$\epsilon_x$ or Lz≧$\epsilon_z$ and Lx≧$\delta_x$ and $L_2$≦$\delta_z$; and (C) Lx>$\delta_x$ or Lz>$\delta_z$. In condition (A), the alignment mechanism I is actuated while the respective amounts of misalignment ΔX, ΔY and ΔZ are used in their present forms without amendment. In condition (B), the alignment mechanism I is actuated through use of the respective amounts of misalignment ΔX', ΔY' and ΔZ', which have been corrected on the basis of the distances Lx and Lz. In condition (C), operation of the alignment mechanism I is stopped.

In the present embodiment, a determination corresponding to step 4 in the first embodiment is omitted. A determination is made as to only whether or not the current state corresponds to condition (C). In a case where the current state corresponds to condition (C), the operation of the alignment mechanism I is stopped in the same manner as in the first embodiment (step 10). In contrast, if the current state does not correspond to condition (C), the respective amounts of misalignment ΔX, ΔY and ΔZ are used in their present forms without amendment, regardless of whether the current state corresponds to condition (A) or (B), thereby moving the optical system housing 3 (step 5).

In a case where the current state corresponds to condition (B), the optical system housing 3 passes through the alignment completion area as a result of automatic actuation, the amount of misalignment must be repeatedly detected and activation of the alignment mechanism I according to the result of computation, must be performed (step 8 and other steps). As a result, it is thought that the time that elapses before the alignment is completed will become longer. However, at the least there may not arise such a delay that would otherwise be caused when an automatic alignment operation is interrupted as a result of the optical system housing 3 moving beyond the alignment detectable range.

In either of the first and second embodiments, the rotary encoders 206 and 306 directly detect the moving distance of the mount 101. Alternatively, the inclination of the joystick 102 may be detected through use of a sensor, and the moving distance of the mount 101 may be determined on the basis of the thus-detected inclination.

<Third Embodiment>

A third embodiment of the present invention will now be described by reference to FIGS. 9 and 10.

An ocular refractive power measuring device according to the third embodiment is substantially identical in structure with that described in the first embodiment. In the first embodiment, the rotary encoders 206 and 306 measure the moving distance of the mount 101. In contrast, in the present embodiment, the frequency or cycle of each of pulse signals output from the rotary encoders 206 and 306 is computed, and the moving speed Vx (in the X direction) and Vz (in the Z direction) of the mount 101 are determined on the basis of the computation results. On the basis of the moving speeds Vx and Vz, the amounts of misalignment ΔX and ΔZ are corrected. The construction of a velocity detection device is already well-known, and hence its explanation is omitted here for brevity. The operation of the ocular refractive power measuring device will be described hereinbelow according to a flowchart shown in FIG. 9.

Figure 9:
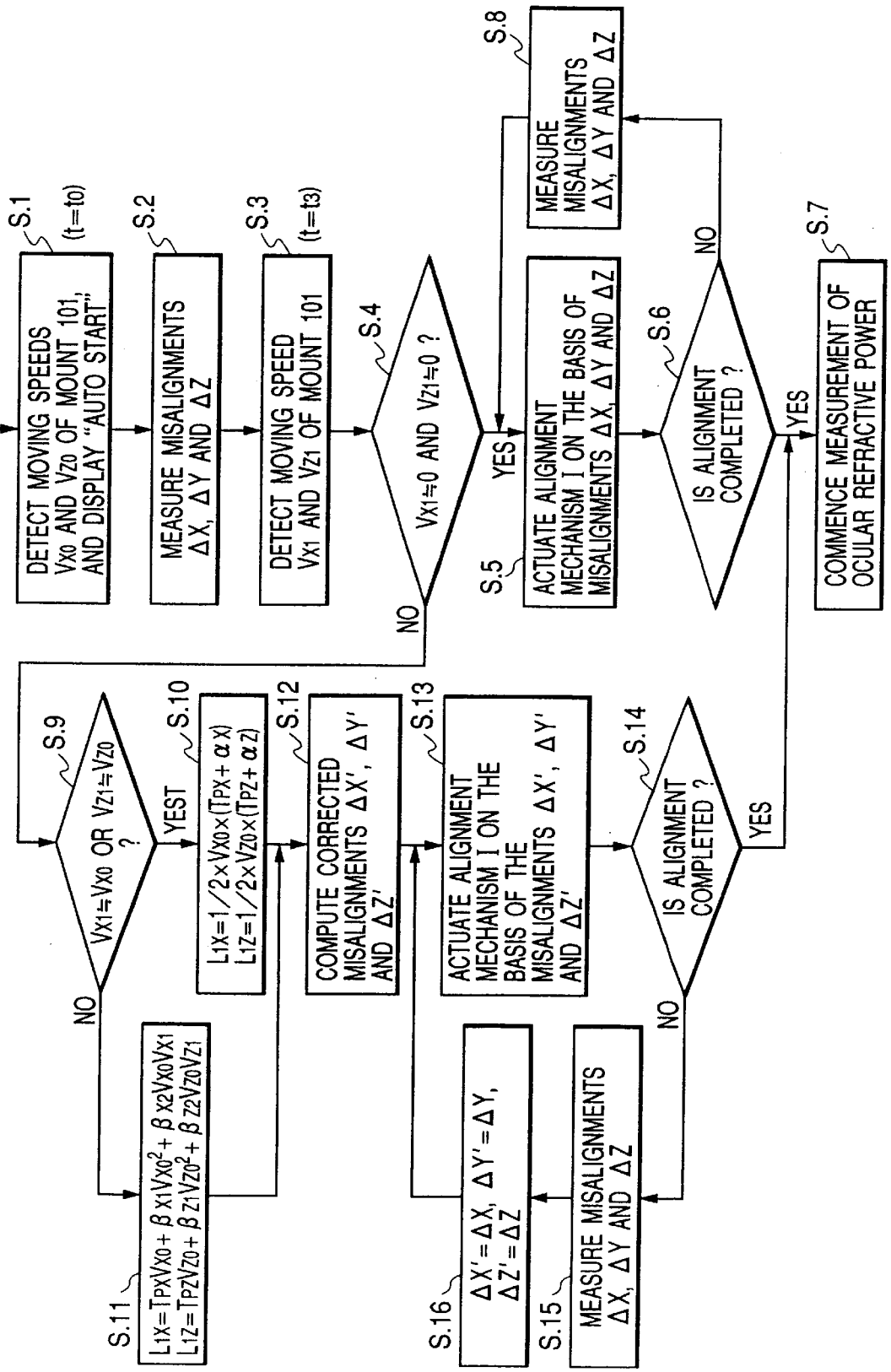
FIG. 9 is a flowchart showing alignment procedures according to a third embodiment of the present invention.

Step 1 (Abbreviated as S1 in FIG. 9, the Same Also Applies to Other Steps)

Prior to Step 1, the operator aligns the main unit section 4 such that the amounts of misalignment ΔX and ΔZ become small, by means of operating the joystick 102. The optical system housing 3 is vertically aligned such that the amount of misalignment ΔY becomes small. When the amounts of misalignment ΔX, ΔY and ΔZ assume a value of 2 mm or less, respectively, processing shifts to step 1, in which the control circuit 81 commences an automatic alignment operation. In step 1 (reference time $t_0$), the control circuit 81 detects the moving speeds of the mount 101 (i.e., Vx=Vxo and Vz=Vzo) on the basis of pulse signals output from the rotary encoders 206 and 306. Message "AUTO START" appears on the monitor 90, thereby notifying the operator of commencement of automatic alignment operation. The present embodiment is based on the assumption that, when the operator becomes aware of the notification and stops operation of the joystick 102, the mount 101 comes to a standstill while decelerating from that moment at a deceleration of −50.0 mm/s².

Step 2

The step is commenced immediately after completion of step 1. In step 2, on the basis of the video signal output from the CCD 28, the control circuit 81 measures the amount of misalignment ΔX, ΔY and ΔZ in the respective X, Y and Z directions at that time.

Step 3

Step 3 is performed at time $t_3$, by which a preset period of time $T_{P2}$ has elapsed since time $t_0$ at which step 1 was performed. In step 3, the control circuit 81 again detects the moving speeds Vx and Vz of the mount 101 in accordance with the pulse signals output from the rotary encoders 206 and 306. The speeds detected in step 3 are obtained as $V_{x1}$ and $V_{z1}$ so as to be distinguished from the speeds Vx and Vz determined in step 1.

Here, the preset period of time $T_{P2}$ is slightly longer than an average value of response times $T_{RE}$. The preset time $TP_2$ is shorter than the preset time $T_{P1}$ described in the first embodiment. Here, on the basis of the assumption that the average value of response time $T_{RE}$ is 150 ms, the preset time $TP_2$ is set to 200 ms.

Step 4

Step 4 is performed immediately after completion of step 3. In step 4, the control circuit 81 makes a determination as to whether or not $V_{x1} \approx 0$ (including $V_{X1}=0$) is satisfied and a determination as to whether or not $V_{z1} \approx 0$ (including $V_{z1}=0$), thereby determining whether or not there is a necessity of correcting the amount of misalignment ΔX or the amount of misalignment ΔZ.

Figure 10:
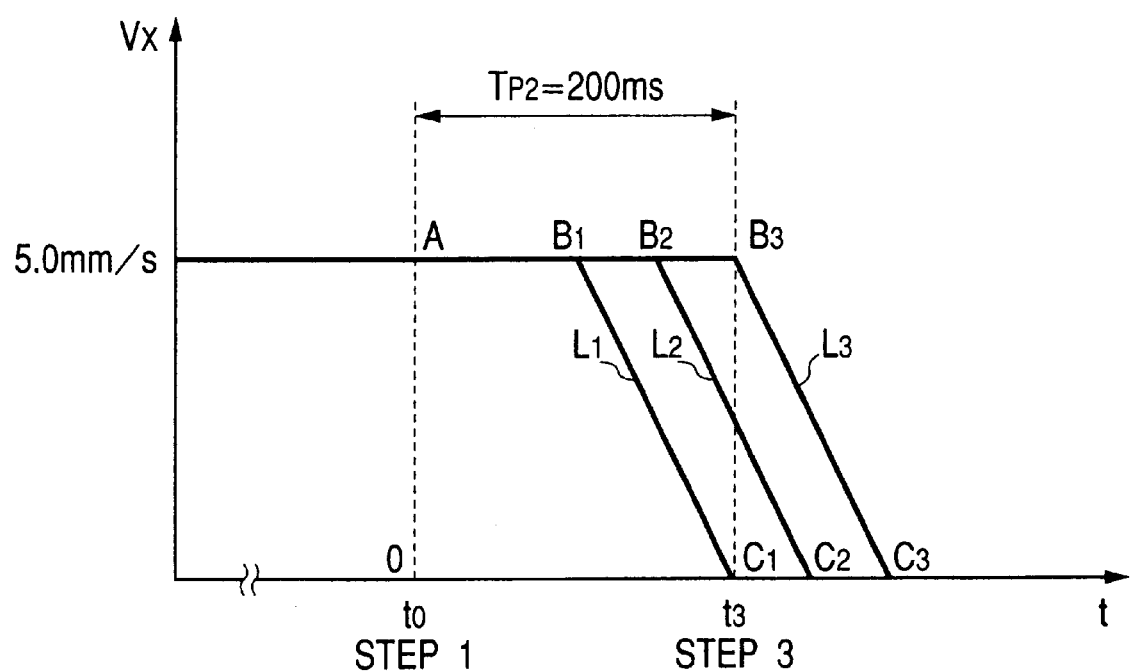
FIG. 10 is a schematic drawing showing an example of a change in the moving speed of a mount according to the third embodiment.

For example, in the case, the moving speed Vxo of the mount 101 at the time at which step 1 is to be performed (i.e., time $t_o$) is 5.0 mm/s, as indicated by line $L_1$ shown in FIG. 10, and the response time $T_{RE}$ is a value of 100 ms shorter than the average value of response time or is a value of less than 100 ms, $V_{x1}$ becomes zero at the time at which step 3 is to be performed (i.e., time $t_3$). A total moving distance $L_{2x}$ over which the mount 101 moves in the X direction is equal to or smaller than a value corresponding to the area of a trapezoid $AB_1C_1O$ shown in FIG. 10; that is, $$\{(100+200)\times10^{-3}\}\times5.0/2=0.75 \text{ (mm)}.$$

As mentioned previously, the alignment completion area is defined as having an allowance of ±0.5 mm in each of the X, Y, and Z directions with reference to a strictly-determined alignment completion position. In a case where the distance Lx over which the mount 101 moves as a result of operation of the joystick 102 falls within the range of allowance, the alignment can be completed by means of a single series of operations, such as detection of misalignment and actuation of the alignment mechanism I, even when the optical system housing 3 is actuated while the amount of misalignment ΔX is used as it is.

In a case where the moving speed Vxo of the mount 101 at a time $t_o$ a value of 5.0 mm/s, as indicated by line $L_2$ shown in FIG. 10, and in a case where the response time $T_{RE}$ is a value of 150 ms equal to the average value, the moving speed of the mount 101 is still a value of 2.5 mm/s at a time $t_3$. Hence, the total moving distance $L_{2x}$ over which the mount 101 has moved becomes a value equal to the area of a trapezoid $AB_2C_2O$; that is, $$\{(150+250)\times10^{-3}\}\times5.0/2=1.0 \text{ (mm)}.$$

Despite a length in the X direction of the alignment completion area being 1.0 mm, if the alignment mechanism I is actuated by the amount of misalignment ΔX which has been determined beforehand by neglect of the total moving distance $L_{2x}$, the optical system housing 3 is moved excessively. There may arise a high possibility that the optical system housing 3 goes beyond the alignment completion area.

The above description also applies to alignment in the Z direction. Hence, in a case where the result of determination made in step 4 shows that $V_{x1} \approx 0$ and $V_{z1} \approx 0$ are satisfied, it is determined that there is no necessity for correcting the misalignments ΔX and ΔZ, and processing proceeds to step 5. In a case where the result of determination made in step 4 shows that at least one of $V_{x1} \approx 0$ and $V_{z1} \approx 0$ is not satisfied, it is determined that there is necessary for correcting the misalignments ΔX and ΔZ, and processing proceeds to step 9.

Step 5

In step 5, the control circuit 81 activates motors 116, 119, and 124 of the alignment mechanism I in accordance with the amounts of misalignment ΔX, ΔY and ΔZ, thereby moving the optical system housing 3 in the X, Y and Z directions by the amounts corresponding to the amounts of misalignment ΔX, ΔY and ΔZ.

Steps 6 Through 8

In step 6, the control circuit 81 makes a determination as to whether or not the alignment has been completed as a result of actuation of the alignment mechanism I performed in step 5. If it is determined that the alignment has been completed, processing proceeds to step 7, in which the measurement of the ocular refractive power is commenced. In contrast, if it is determined that the alignment has not yet been completed, the respective amounts of misalignment $\Delta X$, $\Delta Y$, and $\Delta Z$ are measured in step 8 in the same manner as in step 2. Processing again returns to step 5, to be repeatedly performed according to the same procedures.

Step 9

In step 9, the control circuit 81 makes a determination as to whether $V_{xo} \approx V_{x1}$ (including $V_{xo} = V_{x1}$) or $V_{zo} \approx V_{z1}$ (including $V_{zo} = V_{z1}$) is satisfied. As a result, the control circuit 81 determines whether the amounts of misalignment $\Delta X$ and $\Delta Z$ are corrected in accordance with either step 10 or step 11, which is described later.

The case of $V_{x0} \approx V_{x1}$ is, for example, as indicated by line $L_3$ of FIG. 10, the case the moving speed Vxo of the mount 101 at the time of step 1 (i.e., time $t_o$) is 5.0 mm/s, and the response time $T_{RE}$ is greater than the preset time $T_{P2}$ (=200 ms). In such a case, the total distance $L_{2x}$ over which the mount 101 moves in the X direction is equal to or more than a value corresponding to the area of a trapezoid $AB_3C_3O$ shown in FIG. 10; that is, $$\{(200+300) \times 10^{-3}\} \times 5.0/2 = 1.25 \text{ (mm)}.$$

As mentioned previously, the alignment detectable range is defined so as to have an allowance of ±2.0 mm in each of the X, Y, and Z directions with reference to a strictly-determined alignment completion position. If the alignment mechanism I is actuated by the amount of misalignment $\Delta X$ which has been determined beforehand by neglect of the total moving distance $L_x$, the optical system housing 3 is moved excessively. There may arise a high possibility that the optical system housing 3 goes beyond the alignment detectable range, to stop the automatic alignment.

In a case that neither $V_{x0} \approx V_{x1}$ nor $V_{z0} \approx V_{z1}$ is satisfied; for example, in a case indicated by line $L_2$ of FIG. 10, if the optical system housing 3 is moved by the amount of misalignment $\Delta X$ which has been determined beforehand by neglect of the moving distance $L_x$ of the mount 101, there is a slight possibility that the optical system housing 3 goes beyond the alignment detectable range, in contrast with the case indicated by line $L_3$. However, there still remains a chance that the optical system housing 3 goes beyond the alignment completion area, and there is a high probability that a round of operations, such as detection of the amount of misalignments and actuation of the alignment mechanism I, has to be performed repeatedly several times.

The above description also applies to the alignment in the Z direction. Hence, in a case where the result of determination made in step 9 shows that $V_{xo} \approx V_{x1}$ or $V_{zo} \approx V_{z1}$ is satisfied, processing proceeds to step 10. In a case where the result of determination made in step 9 shows that neither $V_{xo} \approx V_{x1}$ nor $V_{zo} \approx V_{z1}$ is satisfied, processing proceeds to step 11.

Step 10

In step 10, the control circuit 81 computes total moving distances $L_{2x}$ and $L_{2z}$ based on the assumption that the response time $T_{RE}$ is equal to the preset time $TP_2$.

$$L_{2x} = 1/2 \times V_{xo} \times (T_{P2} + \alpha_x)$$

$$L_{2z} = 1/2 \times V_{zo} \times (T_{P2} + \alpha_z)$$

Processing proceeds to step 12, wherein $\alpha_x$ and $\alpha_z$ are constants.

Step 11

In step 11, the control circuit 81 computes total moving distances $L_{2x}$ and $L_{2z}$ through use of constants $\beta_{x1}$, $\beta_{x2}$, $\beta_{z1}$, and $\beta_{z2}$.

$$L_{2x} = T_{P2}V_{xo} + \beta_{x1}V_{xo}^2 + \beta_{x2}V_{xo}V_{x1}$$

$$L_{2z} = T_{P2}V_{zo} + \beta_{z1}V_{zo}^2 + \beta_{z2}V_{zo}V_{z1}$$

Processing proceeds to step 12.

Step 12

In step 12, the control circuit 81 computes the corrected amounts of misalignment $\Delta X'$, $\Delta Y'$, and $\Delta Z'$, by means of substituting the amounts of misalignment $\Delta X$, $\Delta Y$, and $\Delta Z$ computed in step 2 and the total moving distances $L_{2x}$ and $L_{2z}$ computed in step 10 or step 11 into corresponding equations provided below.

$$\Delta X' = \Delta X - L_{2x}$$

$$\Delta Y' = \Delta Y$$

$$\Delta Z' = \Delta Z - L_{2z}$$

Step 13

In step 13, the control circuit 81 activates motors 116, 119, and 124 of the alignment mechanism I in accordance with the amounts of misalignment $\Delta X'$, $\Delta Y'$, and $\Delta Z'$, which are computed by the previous step, to thereby move the optical system housing 3 by the amounts corresponding to the misalignments $\Delta X'$, $\Delta Y'$, and $\Delta Z'$ in the corresponding X, Y and Z directions.

Steps 14 Through 16

In step 14, the control circuit 81 makes a determination as to whether or not the alignment has been completed as a result of actuation of the alignment mechanism I performed in the previous step. If it is determined that the alignment has been completed, processing proceeds to step 7, in which the measurement of the ocular refractive power is commenced. In contrast, if it is determined that the alignment has not yet been completed, the respective amounts of misalignment $\Delta X$, $\Delta Y$, and $\Delta Z$ are measured in step 15 in the same manner as in step 2. In step 16, the respective value of the amounts of misalignment $\Delta X'$, $\Delta Y'$ and $\Delta Z'$ are replaced with the values of misalignment $\Delta X$, $\Delta Y$, and $\Delta Z$ (i.e., $\Delta X' = \Delta X$, $\Delta Y' = \Delta Y$, and $\Delta Z' = \Delta Z$).

Processing again returns to step 13, to be repeatedly performed according to the same procedures.

<Fourth Embodiment>

A fourth embodiment of the present invention will now be described by reference to FIG. 11.

An ocular refractive power measuring device according to the fourth embodiment is identical in structure with that described in connection with the third embodiment. The only difference between the ocular refractive power measuring devices lies in a control program for the control circuit 81. In the third embodiment, the moving speed of the mount 101 is measured directly (without involvement of computation of the moving distance of the mount 101), and the amount of misalignment are corrected on the basis of the result of measurement. In contrast, in the present embodiment, the moving speeds Vx and Vz of the mount 101 are measured directly, and detection of the misalignment and actuation of the alignment mechanism I is started when these speeds become substantially zero. As a result, excessive actuation of the optical system housing 3 can be prevented without involvement of correction of the thus-detected amounts of misalignment. FIG. 11 is a flowchart showing the outline of the control program. A description will be given of the operation thereof in accordance with the flowchart shown in FIG. 11.

Figure 11:
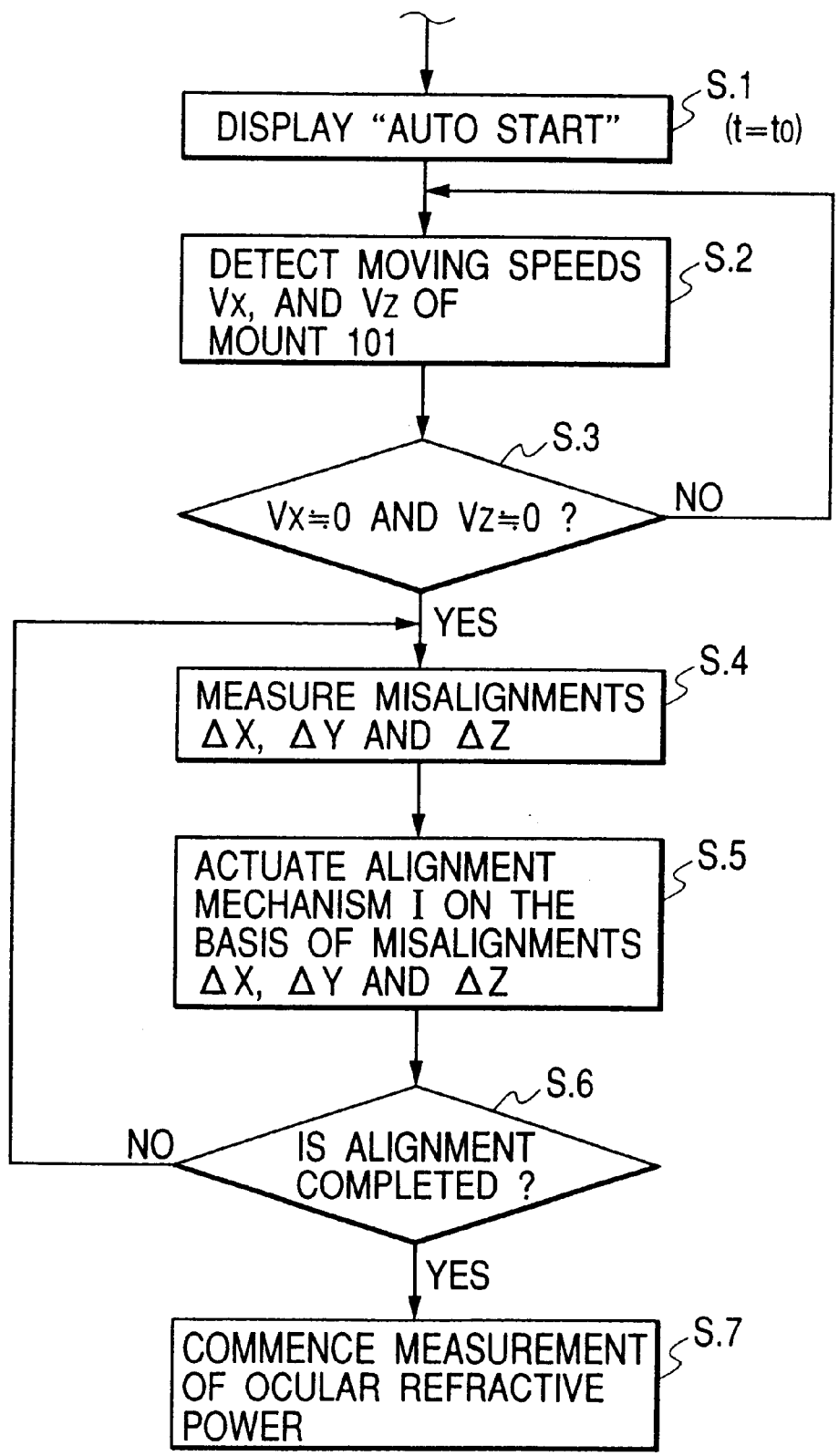
FIG. 11 is a flowchart showing alignment procedures according to a fourth embodiment of the present invention.

Step 1 (Abbreviated as S1 in FIG. 11, the Same Also Applies to Other Steps)

Prior to Step 1, the operator aligns the main unit section 4 such that the amounts of misalignment $\Delta X$ and $\Delta Z$ become small, by means of the operation of the joystick 102. Further, the operator aligns the optical system housing 3 vertically such that the amount of misalignment ΔY becomes small. When the respective amounts of misalignment ΔX, ΔY, and ΔZ are set to be a value of 2 mm or less, respectively, processing shifts to step 1, in which the control circuit 81 commences an automatic alignment operation. In step 1 (reference time $t_0$), the control circuit 81 causes the monitor 90 to display message "AUTO START," thereby notifying the operator of commencement of automatic alignment operation. In this phase, the control circuit 81 does not permit actuation of the alignment mechanism Step 2

In step 2, on the basis of the pulse signals output from the rotary encoders 206 and 306, the control circuit 81 detects the moving speeds Vx and Vz of the mount 101 after a predetermined time (for example, 0.1 second) from time $t_o$ at which step 1 is performed.

Steps 3 and 4

In step 3, a determination is made as to whether or not the moving speeds Vx and Vz of the mount 101 detected in the previous step satisfy Vx≈0 (including Vx=0) and Vz≈0(Vz= 0). In a case where Vx≈0 and Vz≈0 are satisfied, processing proceeds to step 4 and measures the amounts of misalignment ΔX, ΔY, and ΔZ in order to commerce actuation of the alignment mechanism I. If Vx≈0 and Vz≈0 is not satisfied, processing returns to step 2, in which the moving speeds Vx and Vz are detected, to be repeated according to the same procedures.

Step 5

In step 5, the control circuit 81 actuates the motors 116, 119, and 124 of the alignment mechanism I in accordance with the amounts of misalignment ΔX, ΔY, and ΔZ, to thereby move the optical system housing 3 by the amounts corresponding to the amounts of misalignment ΔX, ΔY, and ΔZ in the corresponding X, Y and Z directions.

Steps 6 and 7

In step 6, the control circuit 81 makes a determination as to whether or not the alignment has been completed as a result of actuation of the alignment mechanism I performed in step 5. If it is determined that the alignment has been completed, processing proceeds to step 7, in which the measurement of the ocular refractive power is commenced. In contrast, if it is determined that alignment has not yet been completed, processing returns to step 4, in which the respective amounts of misalignment ΔX, ΔY, and ΔZ are measured. Then, processing is repeatedly performed according to the same procedures.

In the above embodiments, respective steps are performed sequentially. However, the respective steps may be performed in parallel with each other through use of a plurality of CPUs provided in a control circuit. For instance, in the first embodiment, the control circuit 81 may be provided with a first CPU for performing steps 1 and 3 (detection of position of the mount 101) and a second CPU for performing step 2 (i.e., the measurement of the amounts of misalignment ΔX, ΔY, and ΔZ). Thus, processing to steps 1, 2, and 3 may be performed simultaneously.

While only certain embodiments of the invention have been specifically described herein, it will apparent that numerous modifications may be made thereto without departing from the spirit and scope of the invention.

Since the ocular refractive power measuring device according to the present invention has the foregoing construction, the present invention yields an advantage of the ability to avoid occurrence of a delay in the actuation of the main unit, which would otherwise be induced by an overlap between actuation of the main unit performed by an automatic alignment mechanism and actuation of the main unit performed by manual operation means when a mechanical mechanism is adopted as manual operation means.

What is claimed is:

1. An ophthalmological apparatus comprising:
    a main unit section having a movable optical system housing which houses an optical system for shooting or examining an eye to be examined;
    a manual operation unit manually positioning the main unit section;
    an alignment chart projection unit projecting onto the eye an chart luminous flux for alignment;
    a chart detection unit detecting the reflected luminous flux of the chart luminous flux reflected on the eye;
    an alignment unit actuating the optical system housing on the basis of a detection result of the chart detection unit in a case where the main unit section is positioned by the manual operation unit so that the chart detection unit detects the reflected luminous flux, such as to move the optical system housing with respect to the main unit section;
    a position information detection unit detecting information about variations in position of the main unit section caused by the manual operation unit during the operation of the chart detection unit; and
    a correction unit correcting the actuating amount of the optical system housing on the basis of a detection result of the position information detection unit.

2. The ophthalmological apparatus according to claim 1, wherein the position information detection unit detects a moving distance of the main unit section between a predetermined reference time and a time after a preset time has elapsed from the predetermined reference time.

3. The ophthalmological apparatus according to claim 2, further comprising:
    a notice unit noticing an operator that the detection of the chart detection unit is commenced,
    wherein the preset time is set so as to correspond to a period from when a notice is issued from the notice unit until the operator stops the operation of the manual operation unit in response to the notice.

4. The ophthalmological apparatus according to claim 3, wherein the preset time is set to be sufficiently longer than an averaged period from when the notice is issued from the notice unit until the operator stops the operation of the manual operation unit in response to the notice.

5. An ophthalmological apparatus comprising:
    a main unit section having a movable optical system housing which houses an optical system for shooting or examining an eye to be examined;
    a manual operation unit manually positioning the main unit section;
    an alignment chart projection unit projecting onto the eye an chart luminous flux for alignment;
    a chart detection unit detecting the reflected luminous flux of the chart luminous flux reflected on the eye;
    an alignment unit actuating the optical system housing on the basis of a detection result of the chart detection unit in a case where the main unit section is positioned by the manual operation unit so that the chart detection unit detects the reflected luminous flux, such as to move the optical system housing with respect to the main unit section;
    a moving speed detection unit detecting a moving speed of the main unit section caused by the manual operation unit during the operation of the chart detection unit; and
    a correction unit correcting the actuating amount of the optical system housing on the basis of a detection result of the moving speed detection unit.

6. The ophthalmological apparatus according to claim 5, wherein the moving speed detection unit detects a moving speed of the main unit section at a predetermined reference time and a moving speed of the main unit section at a time after a preset time has elapsed from the predetermined reference time.

7. The ophthalmological apparatus according to claim 6, further comprising:

a notice unit noticing an operator that the detection of the chart detection unit is commenced, wherein the preset time is set so as to correspond to a period from when a notice is issued from the notice unit until the operator stops the operation of the manual operation unit in response to the notice.

8. The ophthalmological apparatus according to claim 7, wherein the preset time is set to be slightly longer than an averaged period from when the notice is issued from the notice unit until the operator stops the operation of the manual operation unit in response to the notice unit.

9. An ophthalmological apparatus including:

a main unit section having a movable optical system housing which houses an optical system for shooting or examining an eye to be examined;

a manual operation unit manually positioning the main unit section;

an alignment chart projection unit projecting onto the eye an chart luminous flux for alignment;

a chart detection unit detecting the reflected luminous flux of the chart luminous flux reflected on the eye;

an alignment unit actuating the optical system housing on the basis of a detection result of the chart detection unit in a case where the main unit section is positioned by the manual operation unit so that the chart detection unit detects the reflected luminous flux, such as to move the optical system housing with respect to the main unit section;

a moving speed detection unit detecting a moving speed of the main unit section caused by the manual operation unit during the operation of the chart detection unit; and an actuation permission unit permitting a commencement of the actuation of the optical system housing according to the alignment unit on the basis of a detection result of the moving speed detection unit.

\* \* \* \* \*